(12) United States Patent
Pellinen et al.

(10) Patent No.: US 8,703,537 B2
(45) Date of Patent: Apr. 22, 2014

(54) SYSTEM AND METHOD TO MANUFACTURE AN IMPLANTABLE ELECTRODE

(71) Applicant: NeuroNexus Technologies, Inc., Ann Arbor, MI (US)

(72) Inventors: David S. Pellinen, Ann Arbor, MI (US); Jamille Farraye Hetke, Brooklyn, MI (US); Daryl R. Kipke, Dexter, MI (US); Kc Kong, Ann Arbor, MI (US); Rio J. Vetter, Ypsilanti, MI (US); Mayurachat Ning Gulari, Ann Arbor, MI (US)

(73) Assignee: NeuroNexus Technologies, Inc., Ann Arbor, MI (US)

( * ) Notice: Subject to any disclaimer, the term of this patent is extended or adjusted under 35 U.S.C. 154(b) by 0 days.

(21) Appl. No.: 14/030,069

(22) Filed: Sep. 18, 2013

(65) Prior Publication Data

US 2014/0027888 A1    Jan. 30, 2014

Related U.S. Application Data

(60) Continuation of application No. 13/539,766, filed on Jul. 2, 2012, which is a division of application No. 12/130,828, filed on May 30, 2008, now Pat. No. 8,241,950.

(60) Provisional application No. 60/980,662, filed on Oct. 17, 2007.

(51) Int. Cl.
*H01L 23/48* (2006.01)

(52) U.S. Cl.
USPC ........... 438/106; 257/737; 257/777; 257/787; 257/E23.049; 257/E23.123; 257/E23.124; 438/108; 438/118; 438/124; 438/127

(58) Field of Classification Search
USPC .............. 257/257, 737, 738, 777, 778, 787, 257/E23.049, E23.003, E23.015, E23.116, 257/E23.123, E23.124; 438/48, 106, 108, 438/118, 124, 127, 629, 672, 734, 737
See application file for complete search history.

(56) References Cited

U.S. PATENT DOCUMENTS 3,847,687 A * 11/1974 Davidsohn et al. ........... 438/353
5,506,383 A *  4/1996 Chen ......................... 219/85.22

(Continued)

FOREIGN PATENT DOCUMENTS

JP    07335673         12/1995
JP    07335673 A  *  12/1995

OTHER PUBLICATIONS

Conformal Coating of Surface-Mounting IC, Assignee: Nagl G P [NAGLI], Publication date Oct. 10, 1989.

*Primary Examiner* — Ermias Woldegeorgis
(74) *Attorney, Agent, or Firm* — Michael F. Scalise

(57) ABSTRACT

The method of the preferred embodiments includes the steps of providing a base having a frame portion and a center portion; building a preliminary structure coupled to the base; removing a portion of the preliminary structure to define a series of devices and a plurality of bridges; removing the center portion of the base such that the frame portion defines an open region, wherein the plurality of bridges suspend the series of devices in the open region defined by the frame; and encapsulating the series of devices. The method is preferably designed for the manufacture of semiconductor devices, and more specifically for the manufacture of encapsulated implantable electrodes. The method, however, may be alternatively used in any suitable environment and for any suitable reason.

25 Claims, 7 Drawing Sheets

(56) References Cited

U.S. PATENT DOCUMENTS

| | | | |
|---|---|---|---|
| 5,760,472 A * | 6/1998 | Woodworth et al. | 257/712 |
| 6,114,755 A * | 9/2000 | Ito et al. | 257/675 |
| 6,181,569 B1 * | 1/2001 | Chakravorty | 361/761 |
| 6,600,231 B2 * | 7/2003 | Tominaga | 257/778 |
| 2001/0040262 A1 * | 11/2001 | Uchida et al. | 257/415 |
| 2006/0192230 A1 * | 8/2006 | Wood et al. | 257/234 |

* cited by examiner

SYSTEM AND METHOD TO MANUFACTURE AN IMPLANTABLE ELECTRODE

CROSS-REFERENCE TO RELATED APPLICATIONS

This application is a divisional of U.S. patent application Ser. No. 12/130,828, filed 30 May 2008, now U.S. Pat. No. 8,214,950 to Pellinen et al., which claims the benefit of U.S. Provisional Application No. 60/980,662, filed 17 Oct. 2007 and entitled "Method to Manufacture an Implantable Electrode", which is incorporated in its entirety by this reference.

TECHNICAL FIELD

This invention relates generally to the implantable electrodes field, and more specifically to an improved method to manufacture encapsulated implantable electrodes.

BACKGROUND

Conventional implantable electrodes are coated with dielectrics to provide increased protection from moisture absorption. The majority of encapsulation methods for microfabricated electrodes are completed at the device level, rather than the wafer level, and therefore are more labor intensive and preclude further batch processing of the electrodes. For example, when the devices are encapsulated at the device level, electrode sites must be exposed individually on each device, typically with laser ablation. Alternatively, while some methods do include coating the devices at the wafer level, they involve a layering or "sandwiching" technique that allows for potential fluid leakage between layers. Thus, there is a need for an improved method to manufacture an implantable electrode. This invention provides such an improved and useful method.

DESCRIPTION OF THE PREFERRED EMBODIMENTS

The following description of preferred embodiments of the invention is not intended to limit the invention to these embodiments, but rather to enable any person skilled in the art to make and use this invention.

Figure 6:
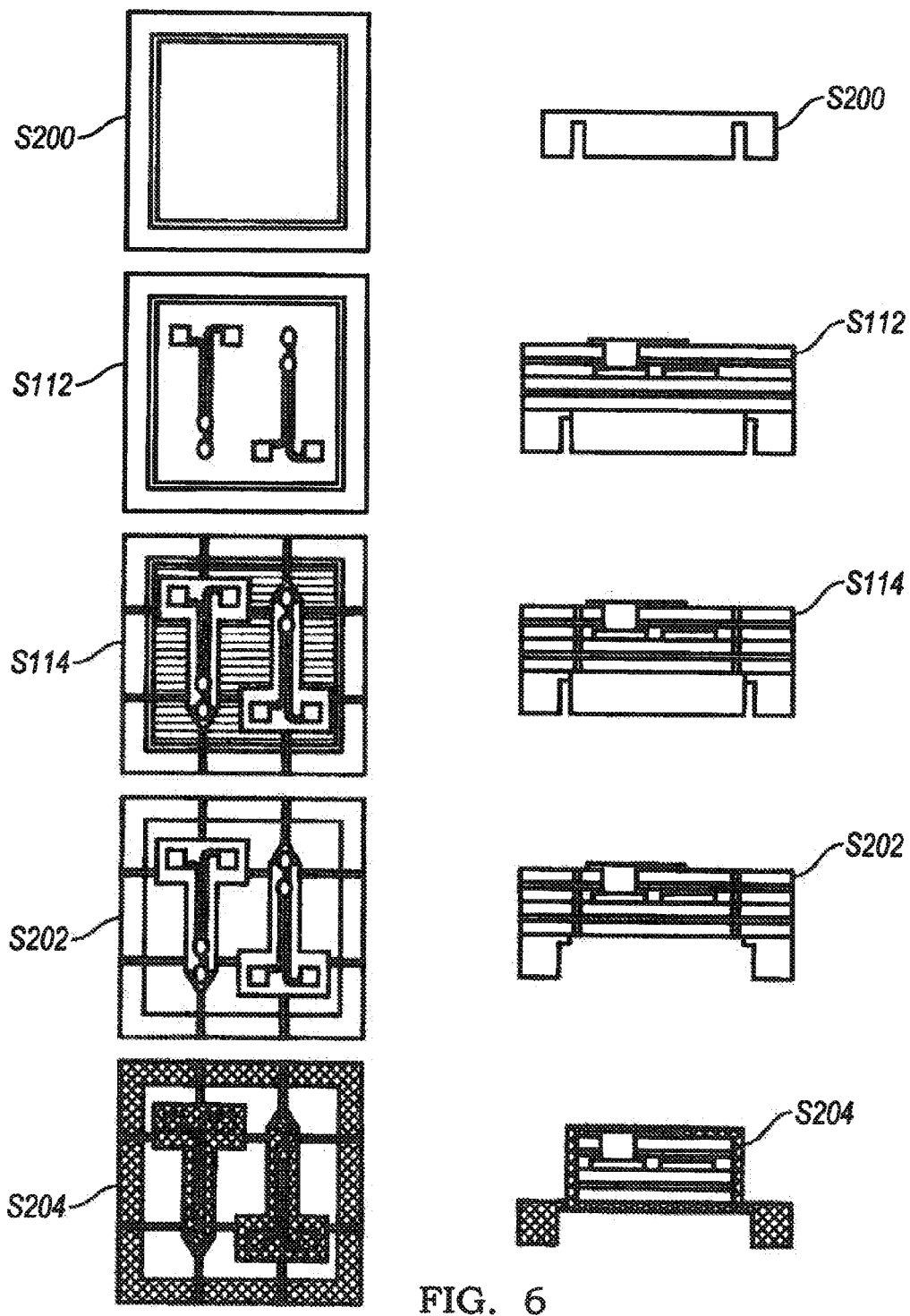
FIG. 6 is a schematic drawing of the method shown as a series of both top views (LEFT) side views (RIGHT) of a portion of the wafer.

As shown in FIG. 6, the method of the preferred embodiments includes the steps of providing a base having a frame portion and a center portion S200; building a preliminary structure coupled to the base S112; removing a portion of the preliminary structure to define a series of devices and a plurality of bridges, wherein the series of devices are coupled to the center portion of the base, and wherein the plurality of bridges are coupled to the frame portion of the base and to the series of devices S114; removing the center portion of the base such that the frame portion defines an open region, wherein the plurality of bridges suspend the series of devices in the open region defined by the frame S202; and encapsulating the series of devices S204. The method is preferably designed for the manufacture of semiconductor devices, and more specifically for the manufacture of encapsulated implantable electrodes. The method, however, may be alternatively used in any suitable environment and for any suitable reason.

Figure 1:
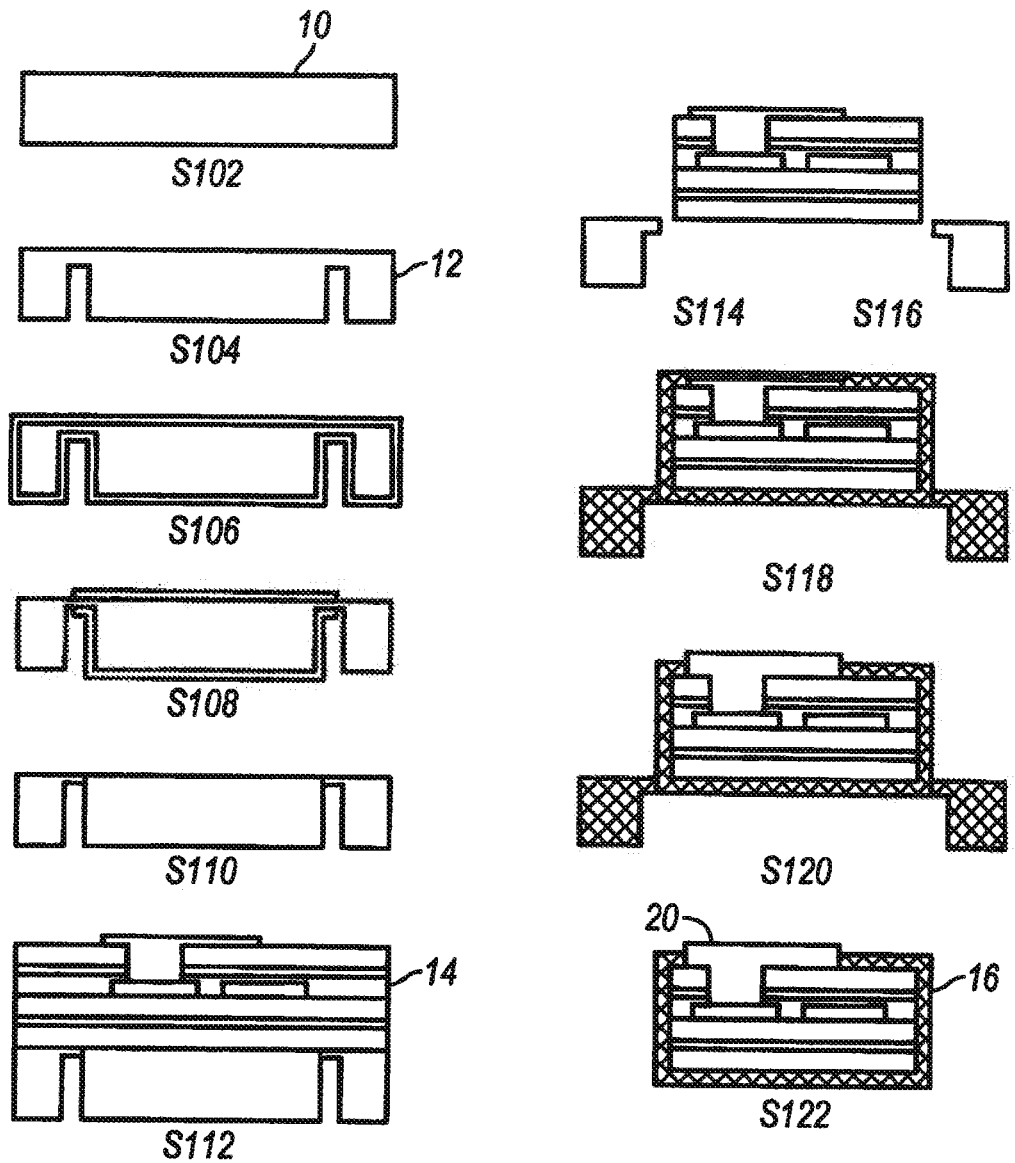
FIG. 1 is a schematic drawing of the method shown as a series of side views of a portion of the wafer.
Figure 2:
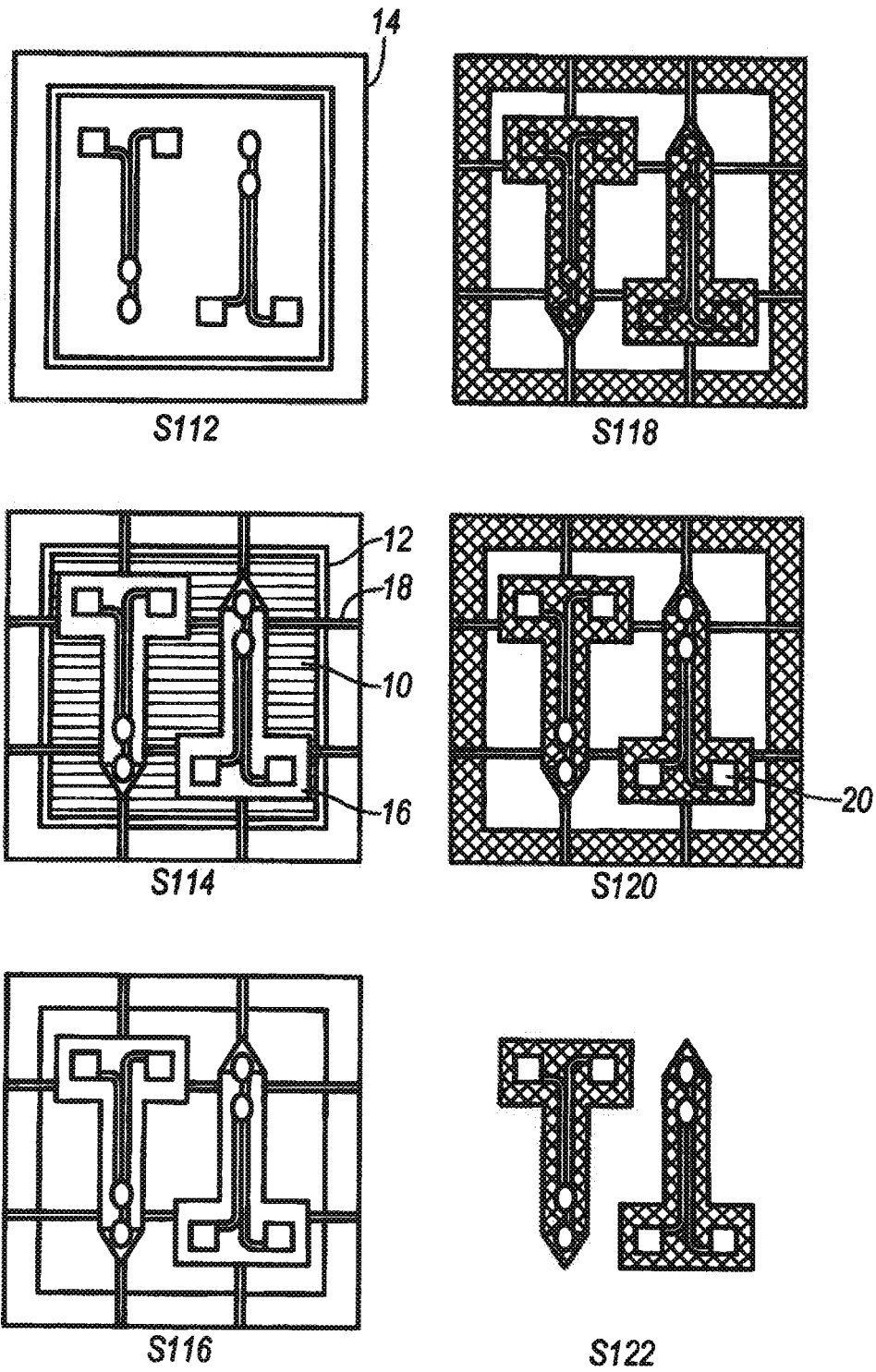
FIG. 2 is a schematic drawing of the method shown as a series of top views of a portion of the wafer.
Figure 3A:
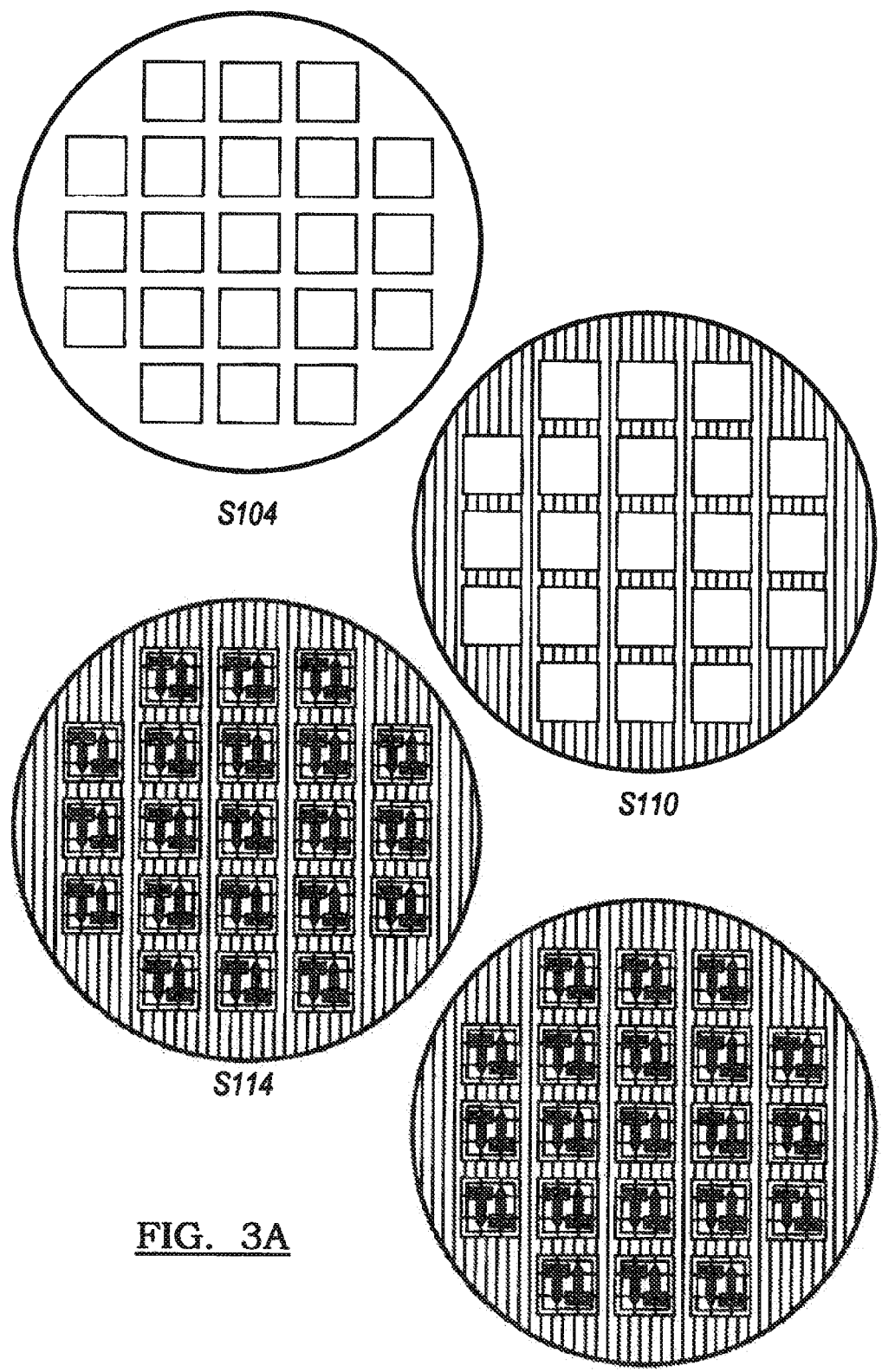
FIGS. 3A and 3B are schematic drawings of the method shown in a series of top views of the wafer.
Figure 3B:
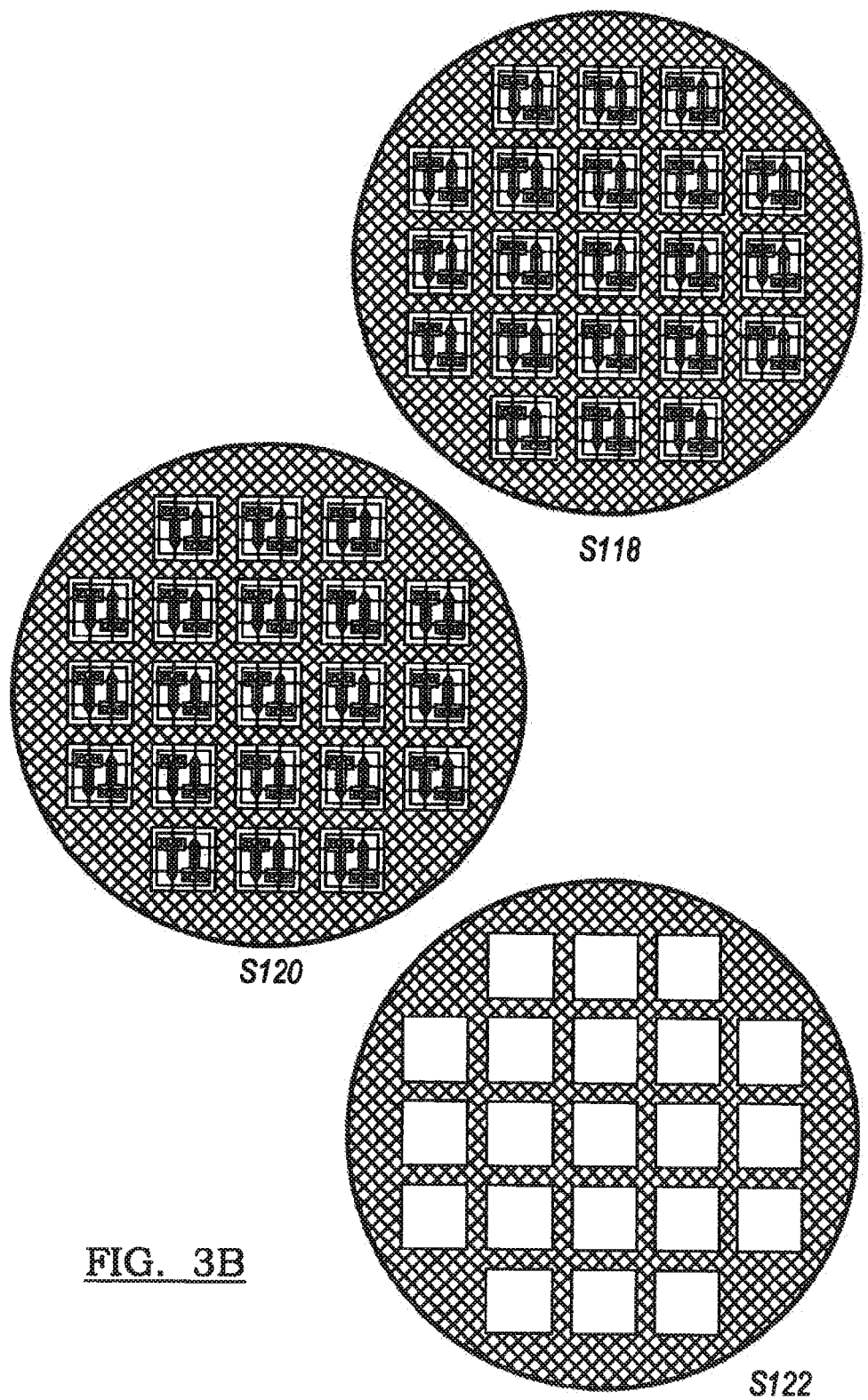
Figure 4:
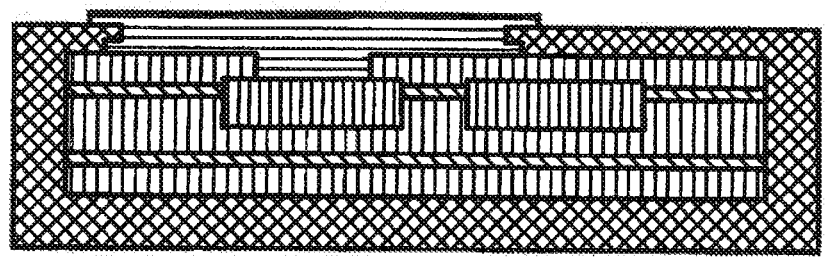
FIGS. 4 and 5 are schematic drawings of a cross section view of a final electrode.

As shown in FIGS. 1-3, step S200, which recites providing a base having a frame portion and a center portion, includes the steps of providing a wafer S102 and removing a portion of the wafer to define a frame S104. Step S202, which recites removing the center portion of the base such that the frame portion defines an open region, includes the steps of creating a mask on the wafer S106; patterning the mask to expose the frame S108; and modifying the frame and removing the remainder of the mask S110; and removing unmodified wafer material S116. Step S204, which recites encapsulating the series of devices, includes the step of encapsulating the devices, the bridges, and the frame S118. The method further includes the steps of removing material to expose sites on the devices S120 and removing the series of devices from the bridges and the frame S122.

Step S102, which recites providing a wafer, functions to provide a wafer 10 upon which to build the series of devices 16. The wafer 10 is preferably a standard wafer conventionally used in semiconductor device fabrication, but may alternatively be any suitable wafer. The wafer 10 is preferably made from silicon, but may alternatively be made from gallium arsenide, indium phosphide, or any other suitable material.

Step S104, which recites removing a portion of the wafer to define a frame, functions to remove a portion of the wafer 10, such that the wafer 10 defines a trench that separates the center wafer portion from the outer frame portion 12 of the wafer 10, as shown in FIG. 1. This step is preferably performed through a deep reactive ion etching (DRIE), but may alternatively be performed through any other suitable removal process, such as other dry etching methods, wet etching, chemical-mechanical planarization, laser etching, or any combination thereof. As shown in step S104 of FIG. 3, multiple portions are preferably removed at the wafer level to define a series of trenches that separate a series of center wafer portions from a series of outer frame portions.

Step S106, which recites creating a mask on the wafer, functions to cover the center wafer portion, the trench, and the outer frame portion 12 in a mask, as shown in step S106 of FIG. 1. The portions of the wafer with the mask will resist modification at later stages of the process, while the unmasked portions are susceptible to modification. The mask is preferably created through oxidation, but may alternatively be created through any suitable process.

Step S108, which recites patterning the mask to expose the frame, functions to remove a portion of the mask to expose a portion of the wafer 10. As shown in step S108 of FIG. 1, the mask is preferably removed from the outer frame portion 12 and remains on the center wafer portion.

Step S110, which recites modifying the frame and removing the remainder of the mask, functions to modify the portions of the wafer where the mask was removed (the masked portions of the wafer remain unmodified) and then to remove all remaining portions of the mask. The modification is preferably deep boron diffusion, but may alternatively be any suitable modification to the unmasked wafer portions. The modification preferably alters the wafer such that the modified portion will behave as an etch stop during later stages of the process. As shown in step S110 of FIG. 1, the outer frame portion is modified while the center wafer portion preferably remains unmodified. As shown in step S110 of FIG. 3, the series of outer frame portions are modified, while the series of center wafer portions preferably remain unmodified. Once the modification is complete, the remainder of the mask is stripped away.

Step S112, which recites building a preliminary structure coupled to the base, functions to build the preliminary structure 14 on the wafer. As shown in step S112 of FIG. 2, at least one preliminary structure 14 is built over the center wafer portion and the outer frame portion. The preliminary structure 14 is preferably one of several variations.

In a first variation, as shown in FIGS. 1-4, the preliminary structure 14 is an electrode structure that includes conductive leads that transfer signals between the electrode sites and the bond pads. The conductive leads are preferably polysilicon or metal, but may alternatively be made out of any suitable material. The first dielectric is preferably an inorganic stack of silicon dioxide, silicon nitride, and silicon dioxide (preferably a tri-layer stack of inorganic dielectrics). The first dielectric stack provides electrical insulation to the underlying conductive leads. Alternatives to the first dielectric include silicon carbide and even other polymers such as polyimide or parylene. The second dielectric may be the same as the first dielectric stack, or may alternatively be a vapor deposited polymer such as parylene, PTFE, other fluoropolymers, silicone, or any other suitable material. The second dielectric provides additional electrical insulation to leads. The electrode structure preferably also includes a site 20. The site 20 is preferably an electrode site such as a recording and/or stimulation site. The site 20 is preferably made from gold, iridium, or platinum, but may alternatively be made from any suitable material. The sites 20 may further include bond pads that provide a point of contact to an external connector. The bond pads are preferably gold, but may alternatively be any suitable material. The preliminary structure 14 in this variation may further include a metal shield that provides extra electrical isolation of the leads from the surrounding environment. The metal shield is preferably titanium, but may alternatively be any suitable material.

Figure 5:
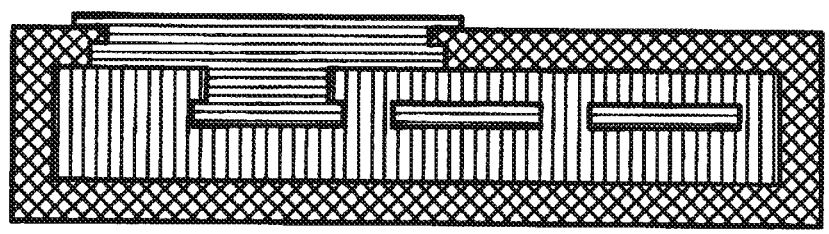

In a second variation, as shown in FIG. 5, the preliminary structure 14 is an electrode structure, which includes a center layer that is preferably metal conductors and sites 20. The metal is preferably platinum, but may alternatively be any other suitable material. The center layer is preferably sandwiched between layers of polyimide. The outer material may alternatively be any other suitable material.

Although the preliminary structure 14 is preferably one of these variations, the preliminary structure 14 may be any suitable device fabricated through any suitable method. The preliminary structure 14 may further be a microfluidic device, a MEMS sensor, a MEMS actuator, or any other suitable wafer level batch fabricated device.

Step S114, which recites removing a portion of the preliminary structure to define a series of devices and a plurality of bridges, functions to remove portions of the preliminary structure 14 such that the remaining portions of the preliminary structure define a series of devices 16 and a series of bridges 18. As shown in step S114 of FIG. 1, a removal process is performed to delineate a series of devices 16 and a series of bridges 18. As shown in FIG. 2, the devices 16 are located generally over the center wafer portion 10' and the bridges 18 function to secure the devices 16 to the outer frame portion. As shown in step S114 of FIG. 3, the series of devices 16 are located generally over the series of center wafer portions and the series of bridges 18 function to secure the devices 16 to the series of outer frame portions. This step is preferably performed through a reactive ion etching (RIE), but may alternatively be performed through any other suitable removal process, such as other dry etching methods, wet etching, chemical-mechanical planarization, laser etching, or any combination thereof.

Step S116, which recites removing unmodified wafer material, functions to remove the unmodified center wafer portion 10' beneath the series of devices 16, while the outer frame portion 12 that was modified in step S110 remains, as shown in step S116 of FIG. 1. The outer frame portion 12 supports the devices 16 suspended by the bridges 18, as shown in FIG. 2. As shown in step S116 of FIG. 3, the series of bridges 18 function to secure the series of devices 16 to the series of outer frame portions 12. This step is preferably a silicon dissolution that removes the unmodified (non boron doped) portions of silicon from the wafer. The removal process is preferably formed with wet etchants for silicon. These etchants may include potassium hydroxide (KOH), Tetramethylammonium hydroxide (TMAH), and any other suitable etchant that functions to remove silicon from the wafer.

Step S118, which recites encapsulating the electrodes, the bridges, and the frame, functions to encapsulate the remaining portions of the structure in a conformal coat. The coating material is preferably a polymer such as parylene, but may alternatively be any suitable material. In this step, the bridges 18 secure the devices 16 in place while the devices 16 are fully encapsulated in the polymer. As shown in step S118 of FIGS. 1-3, the devices 16, the bridges 18, and the outer frame portions 12 are all encapsulated with the coating material.

Step S120, which recites removing material to expose sites on the electrodes, functions to remove the polymer coating from specific regions on the devices 16 such that the sites 20 are exposed, as shown in step S120 in FIGS. 1-3. The sites 20 are preferably exposed using photo-lithography such as a combination of wet and dry etching, but may alternatively be exposed through any other suitable method such as through use of a laser. The exposed sites 20 may further be electroplated or any other suitable post-encapsulation steps. In this step, the bridges 18 secure the devices 16 in place while the devices 16 undergo any suitable post-encapsulation steps.

Step S122, which recites removing the series of electrodes from the bridges and the frame, functions to remove the completed devices 16 from the frames 12. The bridges 18 are preferably cut or removed in any suitable fashion such that each device 16 is a separate device, as shown in step S122 of FIGS. 1 and 2. As shown in FIG. 3, the series of outer frame portions 12 remain once the devices 16 are removed.

The elements of this process may be grouped into microscale elements and macroscale elements. The microscale elements are those that make up the preliminary structure 14 such as the sites 20 (the electrode sites and the bond pads) and the conductive leads. Macroscale elements are those that provide structural support to the device during the steps of the manufacturing method, specifically during the encapsulation and post-encapsulation steps. The macroscale elements include the outer frame portion 12, which allows for suspension of the devices 16 and the bridges 18 which hold the devices 16 within the frame 12 and to each other.

Figure 7A:
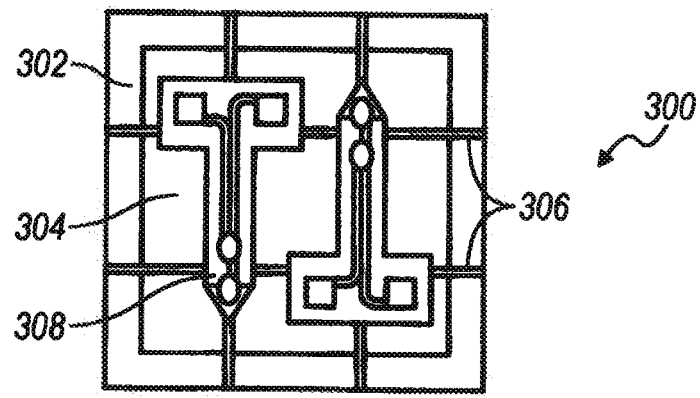
FIGS. 7A, 7B, and 7C, are drawings of the device encapsulation system of the invention.
Figure 7B:
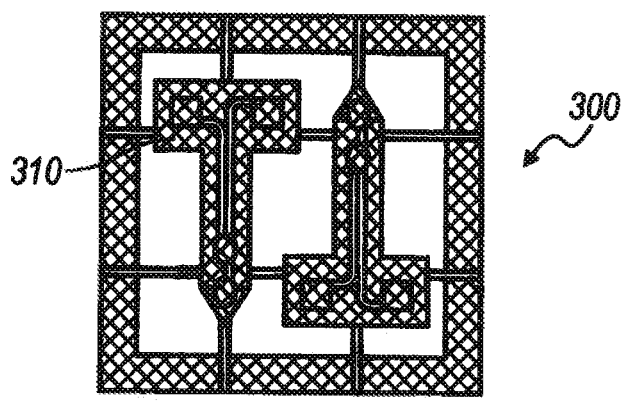
Figure 7C:
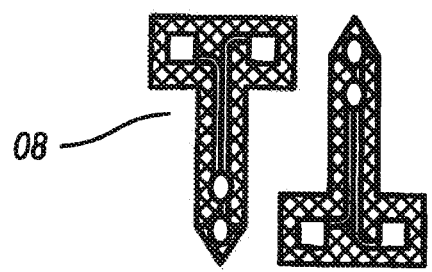

As shown in FIG. 7A, the semiconductor device encapsulation system 300 of the preferred embodiments includes a wafer 302 that defines an open region 304, a plurality of bridges 306 coupled to the wafer 302 that extend from the wafer 302 into the open region 304, and a semiconductor device 308 coupled to the plurality of bridges 306 such that the semiconductor device 308 is suspended in the open region 304. The semiconductor device encapsulation system 300 is preferably designed for the manufacture of semiconductor devices, and more specifically for the manufacture of encapsulated implantable electrodes. The semiconductor device encapsulation system 300, however, may be alternatively used in any suitable environment and for any suitable reason. As shown in FIG. 7B, the semiconductor device encapsulation system 300 further includes a coating 310 that encapsulates the semiconductor device. As shown in FIG. 7C, the semiconductor device 308 is removable from the plurality of bridges such that upon removal, the semiconductor device is encapsulated in a conformal coat of the coating 310.

Although omitted for conciseness, the preferred embodiments include every combination and permutation of the various steps, wafers 10, frames 12, preliminary structures 14, devices 16, bridges 18, sites 20, microscale elements and macroscale elements. Furthermore, any suitable number of preliminary structures and/or devices may be fabricated together. For example, the fabrication may be accomplished via batch processing, preferably on an automated probe station equipped with a laser, but may alternatively be completed with any other suitable equipment.

As a person skilled in the art will recognize from the previous detailed description and from the figures and claims, modifications and changes can be made to the preferred embodiments of the invention without departing from the scope of this invention defined in the following claims.

What is claimed is:

1. An implantable electrode system, comprising:
 a) a wafer comprising a frame portion defining an open region;
 b) at least a first electrode structure comprising a first conductive lead and at least one of a first stimulation electrode site and a first recording electrode site; and
 c) at least a first and a second bridges, the first bridge extending from a first bridge frame end connected to the frame portion to a first bridge electrode end connected to the first electrode structure in the open region, and the second bridge extending from a second bridge frame end connected to the frame portion spaced from the first bridge frame end to a second bridge electrode end connected to the first electrode structure in the open region,
 d) wherein the first electrode structure is connected to the first and second bridges in the open region, spaced from the frame portion to be thereby suspended in the open region defined by the frame portion of the base by the first and second bridges.

2. The implantable electrode system of claim 1 further including:
 a) at least a second electrode structure comprising a second conductive lead and at least one of a second stimulation electrode site and a second recording electrode site;
 b) at least a third and a fourth bridges, the third bridge extending from a third bridge frame end connected to the frame portion to a third bridge electrode end connected to the second electrode structure in the open region, and the fourth bridge extending from a fourth bridge frame end connected to the frame portion spaced from the third bridge frame end to a fourth bridge electrode end connected to the second electrode structure in the open region,
 c) wherein the second electrode structure is connected to the third and fourth bridges in the open region, spaced from the frame portion and from the first electrode structure to be thereby suspended in the open region defined by the frame portion of the base by the third and fourth bridges.

3. The implantable electrode system of claim 2 wherein a fifth bridge extends from a fifth bridge first electrode end connected to the first electrode structure to a fifth bridge second electrode end connected to the second electrode structure to thereby help suspend the first and second electrode structures in a side-by-side relationship in the open region.

4. The implantable electrode system of claim 1 wherein the frame is a wafer.

5. The implantable electrode system of claim 4 wherein the wafer is made of silicon.

6. The implantable electrode system of claim 1 further comprising a coating that encapsulates the first electrode structure.

7. The implantable electrode system of claim 6 wherein the coating further encapsulates the base and the first and second bridges.

8. The implantable electrode system of claim 7 wherein the coating is a conformal coat of a polymer material.

9. The implantable electrode system of claim 7 wherein the coating includes parylene.

10. The implantable electrode system of claim 6 wherein the first electrode structure is removable from the first and second bridges such that upon removal, the first electrode structure is encapsulated in a conformal coat of the coating.

11. The implantable electrode system of claim 1 wherein the first electrode structure comprises a plurality of layers and the first and second bridges comprise the same plurality of layers as the first electrode structure.

12. The implantable electrode system of claim 11 wherein each layer of the plurality of layers of the first electrode structure and of the first and second bridges is selected from the group consisting of silicon, metal, and polymer.

13. The implantable electrode system of claim 1 wherein the first electrode structure comprises a plurality of layers comprising a plurality of conductive leads and a plurality of electrode sites, wherein each electrode site is coupled to a respective conductive lead.

14. The implantable electrode system of claim 1 wherein the conductive lead is disposed adjacent to a dielectric stack that is adapted to provide electrical insulation to the conductive lead.

15. The implantable electrode system of claim 14 wherein the dielectric stack comprises one or more layers of dielectric material selected from the group consisting of silicon, silicon dioxide, silicon nitride, silicon dioxide, silicon carbide, polyimide, parylene, PTFE, silicone.

16. A semiconductor device-system, comprising:
 a) a wafer comprising a frame portion defining an open region;
 b) a first semiconductor device comprising a plurality of layers comprising a conductive lead and a plurality of electrode sites, the plurality of electrode sites comprising at least one of a stimulation electrode site and a recording electrode site coupled to the conductive lead; and
 c) at least a first and a second bridges, the first bridge extending from a first bridge frame end connected to the frame portion to a first bridge semiconductor end connected to the first semiconductor device in the open region, and the second bridge extending from a second bridge frame end connected to the frame portion spaced from the first bridge frame end to a second bridge semiconductor end connected to the first semiconductor device in the open region, d) wherein the first semiconductor device is connected to the first and second bridges in the open region, spaced from the frame portion to be thereby suspended in the open region defined by the frame portion of the base by the first and second bridges.

17. The implantable electrode system of claim 16 further including:
   a) at least a second semiconductor device comprising a second conductive lead and at least one of a second stimulation electrode site and a second recording electrode site;
   b) at least a third and a fourth bridges, the third bridge extending from a third bridge frame end connected to the frame portion to a third bridge semiconductor end connected to the second semiconductor device in the open region, and the fourth bridge extending from a fourth bridge frame end connected to the frame portion spaced from the third bridge frame end to a fourth bridge semiconductor end connected to the second semiconductor device in the open region,
   c) wherein the second semiconductor device is connected to the third and fourth bridges in the open region, spaced from the frame portion and from the first semiconductor device to be thereby suspended in the open region defined by the frame portion of the base by the third and fourth bridges.

18. The implantable electrode system of claim 17 wherein a fifth bridge extends from a fifth bridge first electrode end connected to the first electrode structure to a fifth bridge second electrode end connected to the second electrode structure to thereby help suspend the first and second electrode structures in a side-by-side relationship in the open region.

19. The semiconductor device system of claim 16 further comprising a coating that encapsulates the first semiconductor device.

20. The semiconductor device system of claim 19 wherein the first semiconductor device is removable from the first and second bridges such that upon removal, the first semiconductor device is encapsulated in a conformal coat of the coating.

21. The semiconductor device system of claim 16 wherein the first and second bridges coupled to the first semiconductor device comprise the same plurality of layers as the first semiconductor device.

22. The semiconductor device-system of claim 21 wherein each layer of the plurality of layers of the first semiconductor device and of the first and second bridges is selected from the group consisting of silicon, metal, and polymer.

23. The semiconductor device system of claim 16 wherein the conductive lead is disposed adjacent to a dielectric stack that provides electrical insulation to the conductive lead.

24. The semiconductor device system of claim 23 wherein the dielectric stack comprises one or more layers of dielectric material selected from the group consisting of silicon, silicon dioxide, silicon nitride, silicon dioxide, silicon carbide, polyimide, parylene, PTFE, silicone.

25. A semiconductor device system, comprising:
   a) a wafer comprising a frame portion defining an open region;
   b) at least a first electrode structure comprising a first conductive lead and at least one of a first stimulation electrode site and a first recording electrode site;
   c) at least a first and a second bridges, the first bridge extending from a first bridge frame end connected to the frame portion to a first bridge electrode end connected to the first electrode structure in the open region, and the second bridge extending from a second bridge frame end connected to the frame portion spaced from the first bridge frame end to a second bridge electrode end connected to the first electrode structure in the open region, wherein the first electrode structure is connected to the first and second bridges in the open region, spaced from the frame portion to be thereby suspended in the open region defined by the frame portion of the base by the first and second bridges;
   d) at least a second electrode structure comprising a second conductive lead and at least one of a second stimulation electrode site and a second recording electrode site; and
   e) at least a third and a fourth bridges, the third bridge extending from a third bridge frame end connected to the frame portion to a third bridge electrode end connected to the second electrode structure in the open region, and the fourth bridge extending from a fourth bridge frame end connected to the frame portion to a fourth bridge electrode end connected to the second electrode structure in the open region, wherein the second electrode structure is connected to the third and fourth bridges in the open region, spaced from the frame portion and from the first electrode structure to thereby be suspended in the open region defined by the frame portion of the base by the third and fourth bridges, and
   f) wherein a fifth bridge extends from a fifth bridge first electrode end connected to the first electrode structure to a fifth bridge second electrode end connected to the second electrode structure to thereby help suspend the first and second electrode structures in a side-by-side relationship in the open region.

* * * * *

UNITED STATES PATENT AND TRADEMARK OFFICE
CERTIFICATE OF CORRECTION

PATENT NO.        : 8,703,537 B2
APPLICATION NO.   : 14/030069
DATED             : April 22, 2014
INVENTOR(S)       : David S. Pellinen et al.

It is certified that error appears in the above-identified patent and that said Letters Patent is hereby corrected as shown below:

In the Specification

Column 1, line 7 after the words "This application is a" and before the word "divisional" insert the words --continuation of U.S. Patent Application Serial No. 13/539,766, filed on 2 July 2012, which is a--

Signed and Sealed this
Eighth Day of July, 2014

Michelle K. Lee
*Deputy Director of the United States Patent and Trademark Office*